Oct. 26, 1948. R. L. BYRUM Plant Pat. 809
ROSE PLANT
Filed April 28, 1947
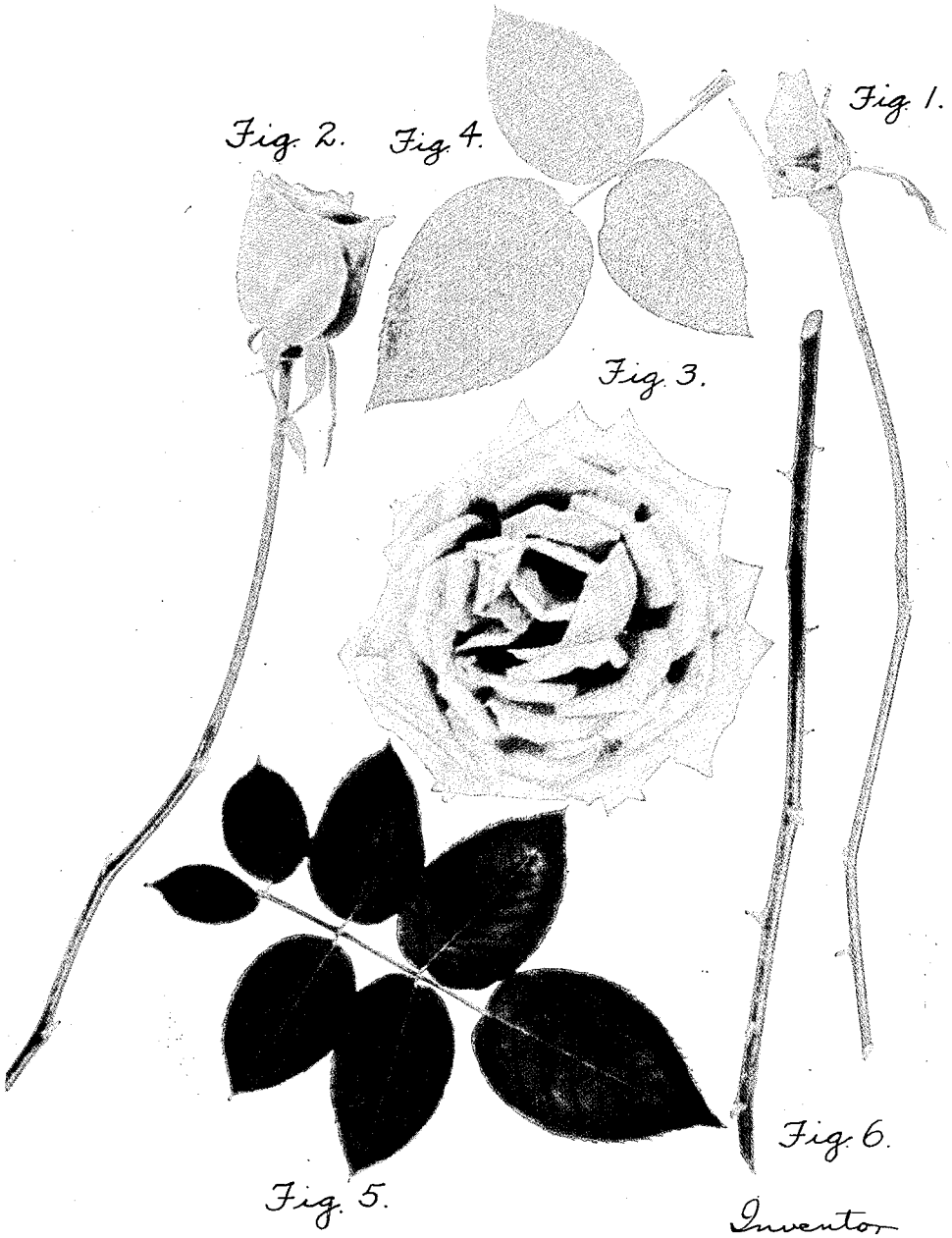
Inventor
R. L. Byrum
By Robb & Robb
Attorneys Patented Oct. 26, 1948

Plant Pat. 809

UNITED STATES PATENT OFFICE

809

ROSE PLANT

Roy L. Byrum, Richmond, Ind., assignor to Joseph H. Hill Company, Richmond, Ind., a corporation of Indiana Application April 28, 1947, Serial No. 744,455

1 Claim. (Cl. 47—61)

The present invention relates to a new and distinct variety of rose plant, resulting from a definite effort to combine certain desirable characteristics of the parents employed to thereby produce a greatly improved rose stock.

In carrying out my objective, I selected an unnamed seedling for the seed parent because of its extra large bloom and good growth habit, but its bloom color was not satisfactory. For the pollen parent, on the other hand, I selected an unnamed seedling because of its extra good bloom color and good foliage, but having only a fair growth habit.

By crossing these two experimental seedlings, I was able to produce a rose plant having the desirable bloom color of the pollen parent and the large size of bloom and growth habit of the seed parent.

Asexual reproduction of this new variety shows the foregoing characteristics come true to form and are established.

In the drawing:

Figure 1 is a detail view of the bud of this new variety, illustrating its long stem and single bloom characteristic;

Figure 2 is a similar view of a specimen as the first petal opens;

Figure 3 is a top view of the bloom at full blown stage, showing the irregular arrangement and color of the very double petals;

Figure 4 is a view of the under side of specimen of the foliage, a compound of three leaf group;

Figure 5 is a view of the upper side of a compound of the seven leaf group produced by the plant; and Figure 6 is a specimen of the plant canes, showing the characteristics of the thorns.

The following is a detailed description of the new variety, color terminology being in accordance with Ridgway's Color Standard, except where otherwise indicated to have ordinary dictionary significance:

Type: Half hardy; tall; bush; greenhouse; seedling; for cut flowers and garden decoration.
Class: Hybrid, Tea.
Breeding: Seedling.
*Seed parent.*—Unnamed seedling.
*Pollen parent.*—Unnamed seedling.
Propagation: Holds its distinguishing characteristics through succeeding propagations by cutting, grafting, and budding.
Locality where grown: Richmond, Indiana.
Flowers borne: Singly to stem, on strong, medium length stems.
Quantity of bloom: Free, in greenhouse.

Continuity: Continuous.
Fragrance: Penetrating; tea.
Bud:
*Peduncle.*—Medium length; medium heavy; erect; medium green; few green hairs.
*Before calyx breaks.*—*Size*—medium. *Form*—long; ovoid, with a conspicuous neck; with foliaceous appendages on the surface of the bud; with foliaceous parts extending beyond the tip of the bud equal to one-half or more of its length.
*As calyx breaks.*—*Color*—between Bordeaux and Burnt Lake, Plate XII.
*As first petal opens.* — *Size* — medium. *Form* — long; pointed. *Color* — outside: Rose Red washed with Pomegranate Purple, Plate XII; inside: velvety red, a brighter color than the outside of the petal, (no corresponding color value found in Ridgway).
*Openings.*—Opens up well.
Bloom: Size, when fully open, medium large—3″ to 4″.
*Petalage.*—Very double; from 35 to 40 petals, arranged irregularly.
*Form.*—Full; globular at first, becoming open; petals remaining at first tightly rolled outward; becoming later, at maturity, loosely rolled outward.
Petals: Thick; with inside shiny and outside satiny.
*Shape.* — Outside — obovate. Intermediate—obovate. Inside—obovate.

This description of a newly opened flower was made from a rose grown in a greenhouse in the month of November, at Richmond, Indiana:

*Color.*—*Outside petal*—outside surface: Tyrian Rose, Plate XII; inside surface: slightly darker than Tyrian Rose with satiny finish. *Intermediate petal*—outside surface: Tyrian Rose, Plate XII; inside surface: slightly darker than Tyrian Rose. *Inner petal*—outside surface: Tyrian Rose, Plate XII; inside surface: slightly darker than Tyrian Rose, Plate XII.

This description was made from a rose that was open for three days in a greenhouse in the month of November, at Richmond, Indiana:

*Color.*—*Outside petal*—outside surface: Rose Color, Plate XII; inside surface: slightly darker than Rose Color, Plate XII. *Inside petal*—outside surface: Rose Color, Plate XII; inside surface: slightly darker than Rose Color, Plate XII.

*General color effect.*—Newly opened flower—Rose Color, Plate XII. Three days open—slightly darker than Rose Color, Plate XII.

*Behavior.*—Persist.

*Flower longevity.*—Cut roses grown in greenhouse kept at living-room temperatures 4 to 5 days in November.

*Reproductive organs*

Stamens: Medium number; arranged regularly about pistils.

Filaments: Medium length; reddish; most with anthers.

Anthers: Medium size; yellow; all open at once.

Pollen: Abundant; gold.

Pistils: Many.

Styles: Very uneven; medium length; medium heavy; bunched.

Stigma: Red.

Ovaries: Some protruding from calyx.

Sepals: Permanent; long; spear-shaped; curled.

*Color*—inside: light Cress Green, Plate XXXI, with white fuzz; outside: Cress Green, Plate XXXI.

*Plant*

Foliage:

*Leaves.*—Compound of three, five or seven leaflets; abundant; large; heavy.

*Leaflets.*—Shape, ovoid with apex obtuse; base round; margin simply serrate.

*Color.*—*Mature*—upper surface: dark green; under surface: very light green. Young—upper surface: light bronze; under surface: very light bronze.

*Rachis.*—Heavy; upper side grooved with under side extremely smooth.

*Stipules.*—Very short; very narrow; with short points turning out at an angle of less than 45°.

*Disease.*—Resistant to mildew and black-spot.

Growth:

*Habit.*—Upright; branched.

*Growth.*—Free.

*Canes.*—Medium heavy.

*Main stems.* — Green brown. *Thorns*—few; short; hooked downward; with short round base. *Prickles*—none. *Hairs*—none.

*Branches.* — Bright green. *Thorns* — few; short; hooked downward; with short narrow base. *Prickles*—none. *Hairs*—none.

*New shoots.*—Green bronze. *Thorns*—few; short; hooked downward; with narrow base. *Prickles*—none. *Hairs*—none.

I claim:

A new and distinct variety of hybrid tea rose plant characterized as to novelty by its good growth habit, its good disease-resistant foliage, and the large size and color of its very double blooms, substantially as shown and described.

ROY L. BYRUM.

No references cited.